United States Patent
Fritzinger et al.

(10) Patent No.: US 8,795,287 B2
(45) Date of Patent: Aug. 5, 2014

(54) TARGETING DEVICE

(75) Inventors: Daniel D. Fritzinger, Warsaw, IN (US);
Daniel W. Buehler, Warsaw, IN (US);
Rebecca Parrott, Warsaw, IN (US);
Michael A. Kay, Peru, IN (US)

(73) Assignee: Zimmer, Inc., Warsaw, IN (US)

( * ) Notice: Subject to any disclaimer, the term of this patent is extended or adjusted under 35 U.S.C. 154(b) by 1580 days.

(21) Appl. No.: 12/028,077

(22) Filed: Feb. 8, 2008

(65) Prior Publication Data

US 2008/0281331 A1    Nov. 13, 2008

Related U.S. Application Data

(60) Provisional application No. 60/888,843, filed on Feb. 8, 2007.

(51) Int. Cl.
*A61B 17/58* (2006.01)
*A61B 17/60* (2006.01)
*A61F 2/00* (2006.01)
*A61B 17/17* (2006.01)

(52) U.S. Cl.
CPC ......... *A61B 17/1725* (2013.01); *A61B 17/1703* (2013.01)
USPC .................. 606/98; 606/99; 606/96

(58) Field of Classification Search
CPC .................. A61B 17/1703; A61B 17/1725
USPC .................. 606/98, 96, 99
See application file for complete search history.

(56) References Cited

U.S. PATENT DOCUMENTS

| 4,881,535 A | | 11/1989 | Sohngen |
| 4,978,351 A | | 12/1990 | Rozas |
| 5,034,013 A | | 7/1991 | Kyle et al. |
| 5,041,119 A | | 8/1991 | Grigg et al. |
| 5,178,621 A | * | 1/1993 | Cook et al. .................. 606/96 |
| 5,308,337 A | | 5/1994 | Bingisser |
| 5,334,192 A | | 8/1994 | Behrens |
| 5,403,321 A | * | 4/1995 | DiMarco .................. 606/96 |
| 5,429,641 A | | 7/1995 | Gotfried |
| 5,498,256 A | | 3/1996 | Furnish |
| D383,539 S | | 9/1997 | Croley |
| D385,350 S | | 10/1997 | Furnish |

(Continued)

FOREIGN PATENT DOCUMENTS

| CA | 964149 A1 | 3/1975 |
| DE | 3205404 A1 | 9/1983 |

(Continued)

OTHER PUBLICATIONS

Howmedica, Surgical Technique for Gamma Locking Nail, 20 pages, available on or before 2001.

(Continued)

*Primary Examiner* — David Bates
(74) *Attorney, Agent, or Firm* — Schwegman Lundberg & Woessner, P.A.

(57) ABSTRACT

A targeting device used in the insertion of an intramedullary nail into a bone. The targeting device includes a guide barrel having a frame portion formed of a non-radiolucent material. The guide barrel also includes a radiolucent material molded over the frame. In addition, the frame includes openings configured to allow a surgeon to view a relatively greater area around the guide barrel in an image of the assembly during surgery.

9 Claims, 18 Drawing Sheets

(56) References Cited

U.S. PATENT DOCUMENTS

| | | |
|---|---|---|
| 6,036,696 A | 3/2000 | Lambrecht et al. |
| 6,210,415 B1 | 4/2001 | Bester |
| 6,214,013 B1 | 4/2001 | Lambrecht et al. |
| 6,387,100 B1 | 5/2002 | Lindequist |
| 6,520,969 B2 | 2/2003 | Lambrecht et al. |
| 6,652,552 B2 | 11/2003 | DuMontelle |
| 6,869,434 B2 | 3/2005 | Choi |
| 7,077,847 B2 | 7/2006 | Pusnik et al. |
| 7,083,624 B2 | 8/2006 | Irving |
| 7,506,908 B2 | 3/2009 | Metcalfe |
| 7,763,027 B2 | 7/2010 | Irving |
| 7,887,545 B2 | 2/2011 | Fernandez et al. |
| 2002/0133172 A1 | 9/2002 | Lambrecht et al. |
| 2003/0023258 A1 | 1/2003 | DuMontelle |
| 2004/0199195 A1 | 10/2004 | Dumontelle |
| 2005/0027304 A1 | 2/2005 | Leloup et al. |
| 2006/0020288 A1 | 1/2006 | Leonard |
| 2006/0098851 A1 | 5/2006 | Shoham et al. |
| 2006/0106400 A1 | 5/2006 | Fernandez et al. |
| 2007/0083213 A1 | 4/2007 | Siravo et al. |
| 2007/0276404 A1 | 11/2007 | Ferrari et al. |
| 2008/0039857 A1 | 2/2008 | Giersch et al. |
| 2008/0039866 A1 | 2/2008 | Stetz et al. |
| 2008/0058829 A1 | 3/2008 | Buscher et al. |
| 2008/0281330 A1 | 11/2008 | Ferrante et al. |
| 2008/0287959 A1 | 11/2008 | Quest et al. |
| 2009/0131951 A1 | 5/2009 | Fernandez |
| 2009/0240253 A1 | 9/2009 | Murray |
| 2010/0030065 A1 | 2/2010 | Farr et al. |
| 2010/0152740 A1 | 6/2010 | O'Reilly et al. |
| 2010/0191225 A1 | 7/2010 | Leonard |
| 2011/0054474 A1 | 3/2011 | Metzinger et al. |
| 2011/0054475 A1 | 3/2011 | Metzinger et al. |
| 2011/0054550 A1 | 3/2011 | Metzinger et al. |
| 2011/0077657 A1 | 3/2011 | Karasik |
| 2011/0112639 A1 | 5/2011 | Regala et al. |
| 2011/0125200 A1 | 5/2011 | Hanson et al. |
| 2011/0130765 A1 | 6/2011 | Fernandez et al. |

FOREIGN PATENT DOCUMENTS

| | | |
|---|---|---|
| EP | 0405132 A1 | 1/1991 |
| EP | 2049025 B1 | 1/1991 |
| EP | 0428452 A1 | 5/1991 |
| EP | 0496950 A1 | 8/1992 |
| EP | 0281763 B1 | 12/1992 |
| EP | 0755660 A2 | 1/1997 |
| GB | 2163074 A | 2/1986 |
| GB | 2401503 B | 5/2005 |
| JP | 3280631 | 9/1999 |
| JP | 2005-013347 A | 1/2005 |
| SU | 1323095 A1 | 7/1987 |
| WO | WO01/89395 A2 | 11/2001 |
| WO | WO03/065907 A1 | 8/2003 |
| WO | WO2008/017501 A1 | 2/2008 |
| WO | WO2009/036162 A1 | 3/2009 |
| WO | WO2009/118733 A2 | 10/2009 |
| WO | WO2010/025575 A1 | 3/2010 |
| WO | WO2011/028520 A2 | 3/2011 |

OTHER PUBLICATIONS

Introduction of Smith-Peterson Pin, 4 pages, published Jul. 1937 in the Lancet, A Journal of British and Foreign Medicine, Surgery, Obstetrics, Pysiology, Chemistry, Pharmacology, Public Health and News.
Smith & Nephew Surgical Technique for Trigen Intertan Intertrochanteric Antegrade Nail, 52 pages, Apr. 2006.
Zimmer ITST Intertrochanteric/Subtrochanteric Fixation IM Nail System Surgical Technique, 28 pages, 2005.
Stryker, Surgical Technique for Gamma3 Nail, 48 pages, 2004.

* cited by examiner

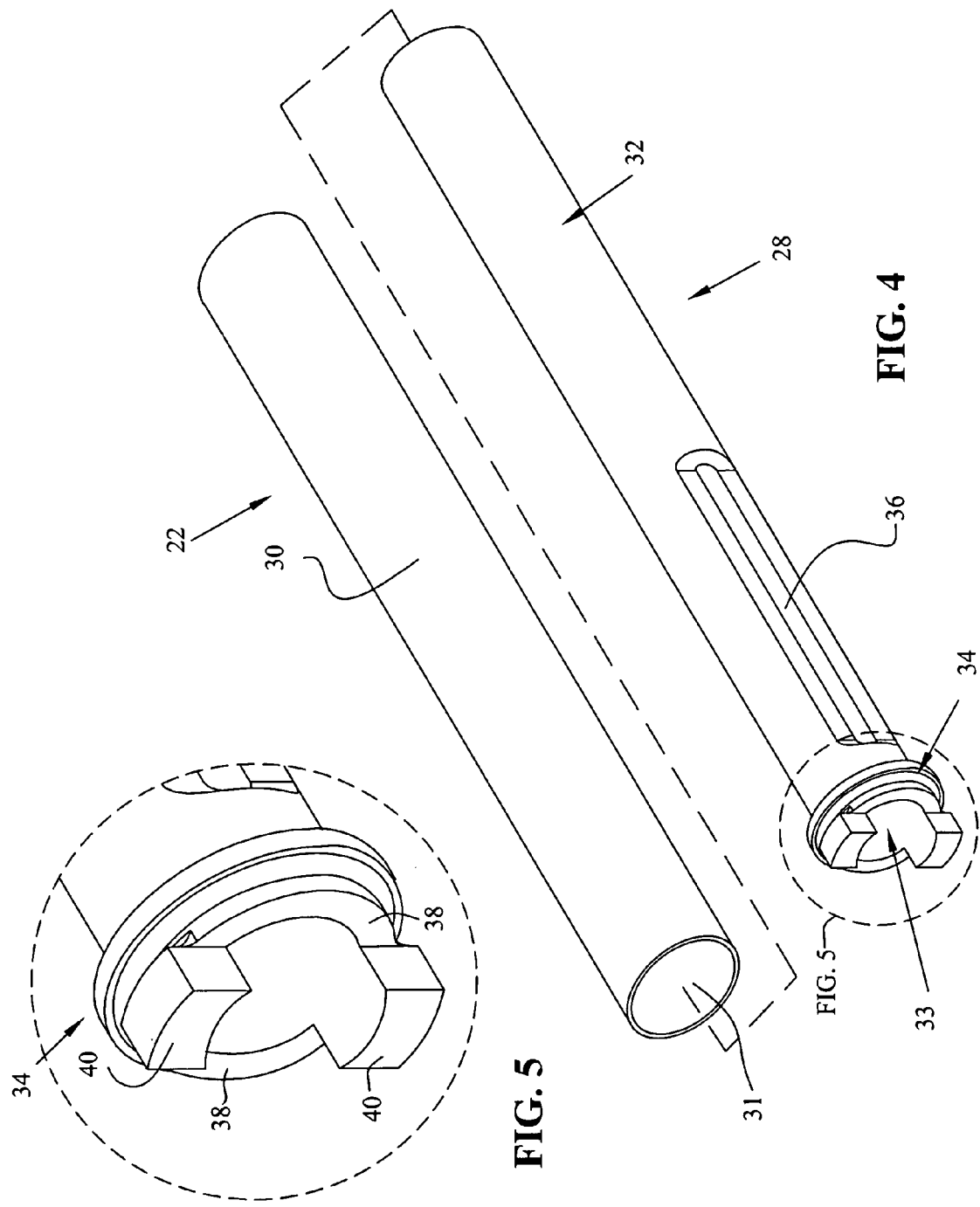

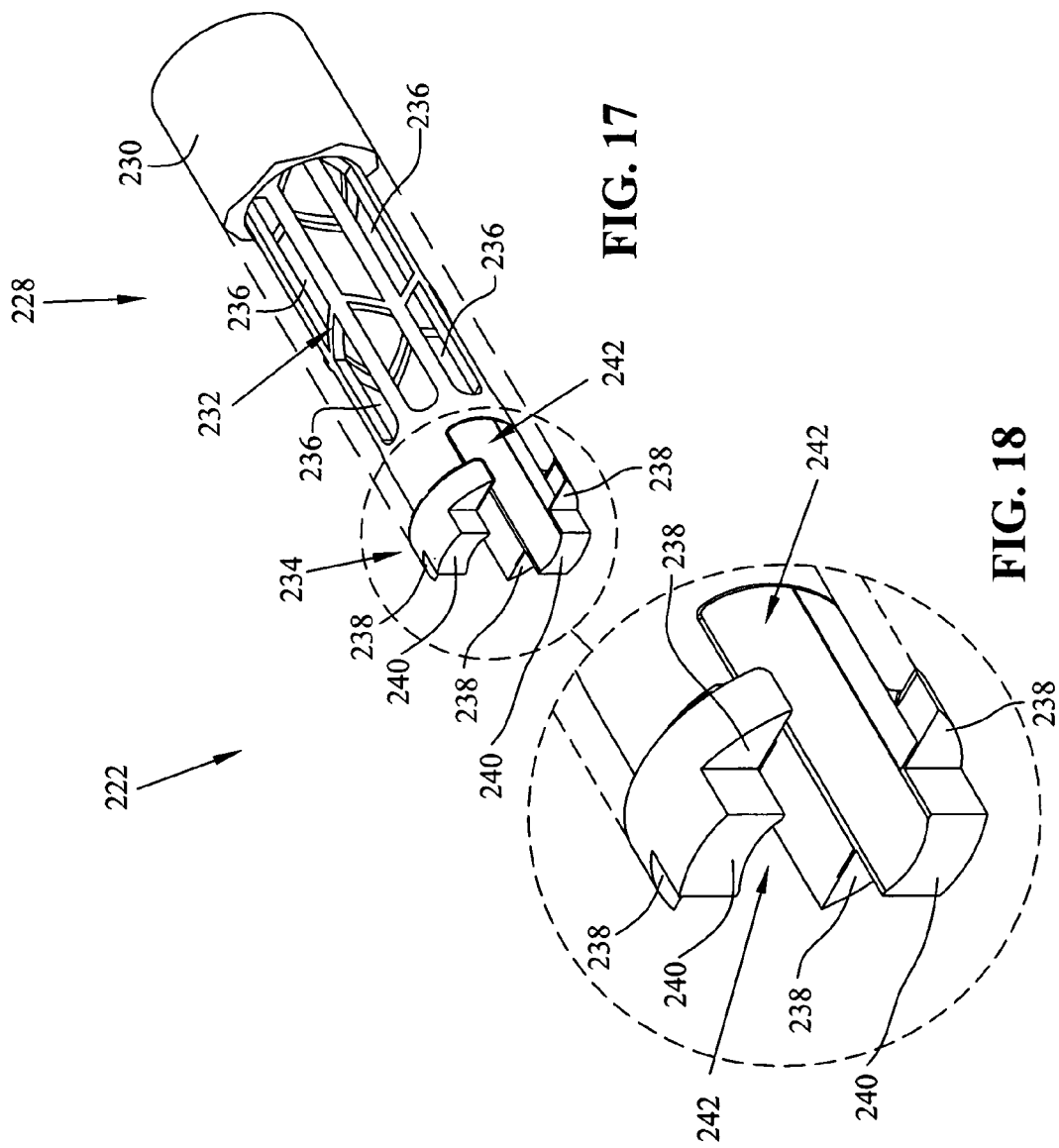

TARGETING DEVICE

CROSS-REFERENCE TO RELATED APPLICATIONS

The present application claims priority to U.S. Provisional Patent Application Ser. No. 60/888,843, filed Feb. 8, 2007, the entire disclosure of which is incorporated by reference herein.

BACKGROUND

1. Field of the Invention

The present invention relates to a targeting device for use in connection with the insertion of an intramedullary nail into an intramedullary canal.

2. Description of the Related Art

Surgeons often use locking intramedullary nails in order to secure a fracture of a long bone such as a femur. Once the nail has been inserted into the intramedullary canal of the bone, a plurality of screws may be driven into the bone and through the nail in a direction transverse to the longitudinal axis of the nail. In order to align the screws with openings formed in the nail, a targeting device may be attached to the proximal portion of the nail. Generally, radiographic imaging may be utilized during the procedure in order to facilitate the proper alignment of the screws prior to a drilling through the bone. Various guides have been developed in order to facilitate proper alignment of the screws with the nail.

SUMMARY

The present invention relates to a targeting device configured to be connected to the proximal end of an intramedullary nail. The targeting device may be utilized in aligning a boring device with transverse bores of the intramedullary nail after the nail has been seated within the intramedullary canal of a patient.

An embodiment of the targeting device may comprise a handle member and a guide barrel. The handle member may include a throughbore, and the guide barrel may extend through the through bore. The guide barrel may have an end configured to be connected to an intramedullary nail. In embodiments of the invention, the guide barrel may include a frame and an overmolding encompassing the frame.

In embodiments of the invention, the frame of the guide barrel may be formed from metal, and the overmolding may be comprised of a radiolucent material, such as, for example, reinforced polyetheretherketone (PEEK).

In embodiments of the invention, the end of the guide barrel may include a plurality of prongs, at least one impact surface, and a recessed area.

In embodiments of the invention, the handle portion may be formed from a radiolucent material, and may include at least one visualization window formed therein.

In one form, the present invention provides a targeting device configured for connection to the proximal end of an intramedullary nail, the targeting device including a handle member and a guide barrel connected to the handle member, the guide barrel having an end adapted to interface with the intramedullary nail, the guide barrel including a frame and sleeve encompassing the frame.

In another form, the present invention provides a targeting device for use during insertion of an intramedullary nail into an intramedullary canal of a patient, the targeting device including a handle portion including a throughbore; and a means for connecting the handle portion with the intramedullary nail which is at least partially formed from at least one radiolucent material.

In another form, the present invention provides a guide barrel configured to engage an intramedullary nail including a frame portion at least partially formed of a non-radiolucent material; and a sleeve at least partially formed of a radiolucent material, the sleeve at least partially encompassing the frame portion; wherein the frame portion includes at least one void.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 4 is a perspective view of a component utilized in the targeting device shown in FIG. 1;

FIG. 5 is an enlarged fragmentary view of a portion of the component shown in FIG. 4;

FIG. 17 is a perspective view of another embodiment of a guide barrel that may be utilized in the targeting device of FIG. 1;

FIG. 18 is an enlarged fragmentary view of a portion of the frame depicted in FIG. 14;

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION

Figure 1:
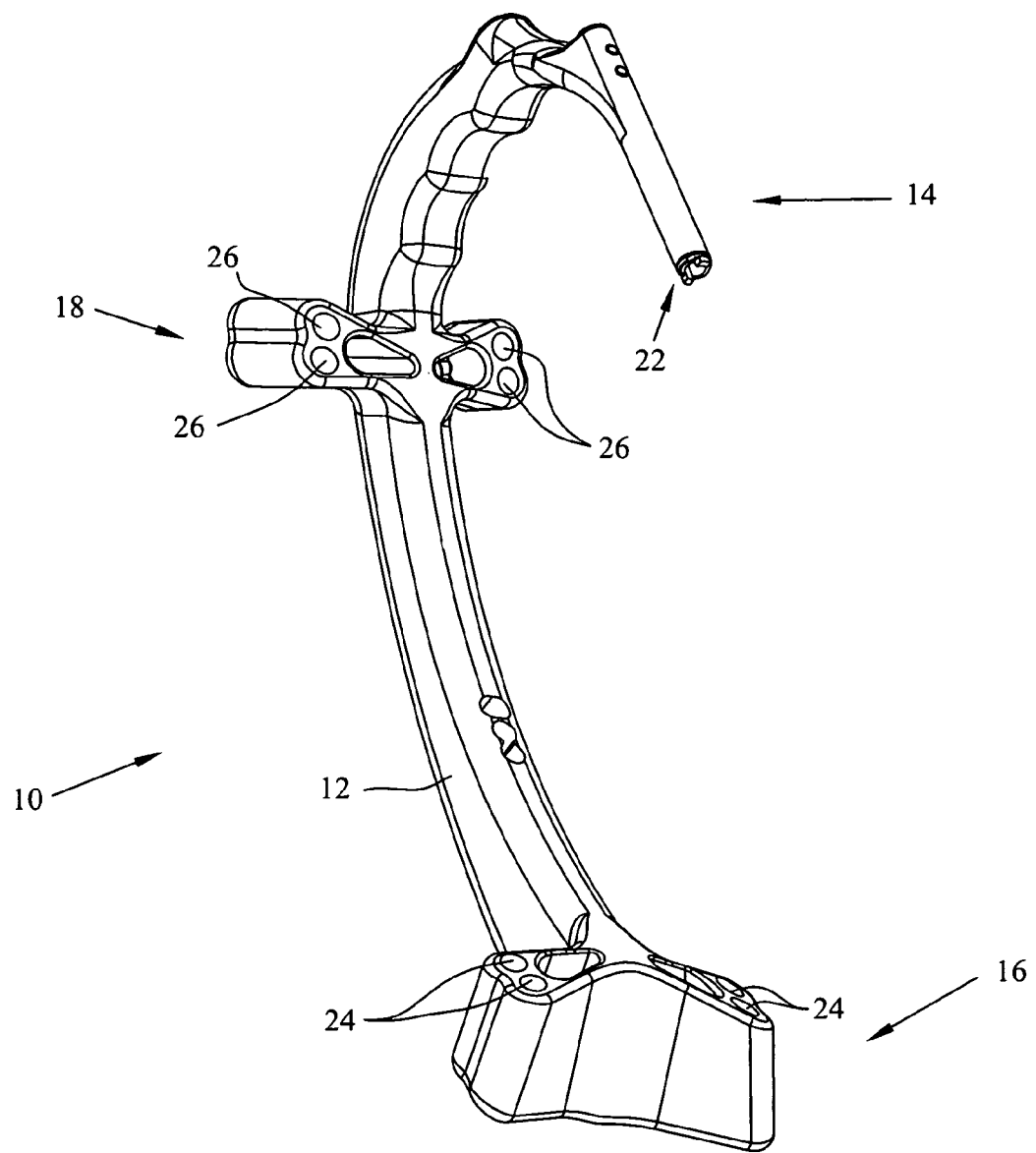
FIG. 1 is a perspective view of a targeting device.
Figure 2:
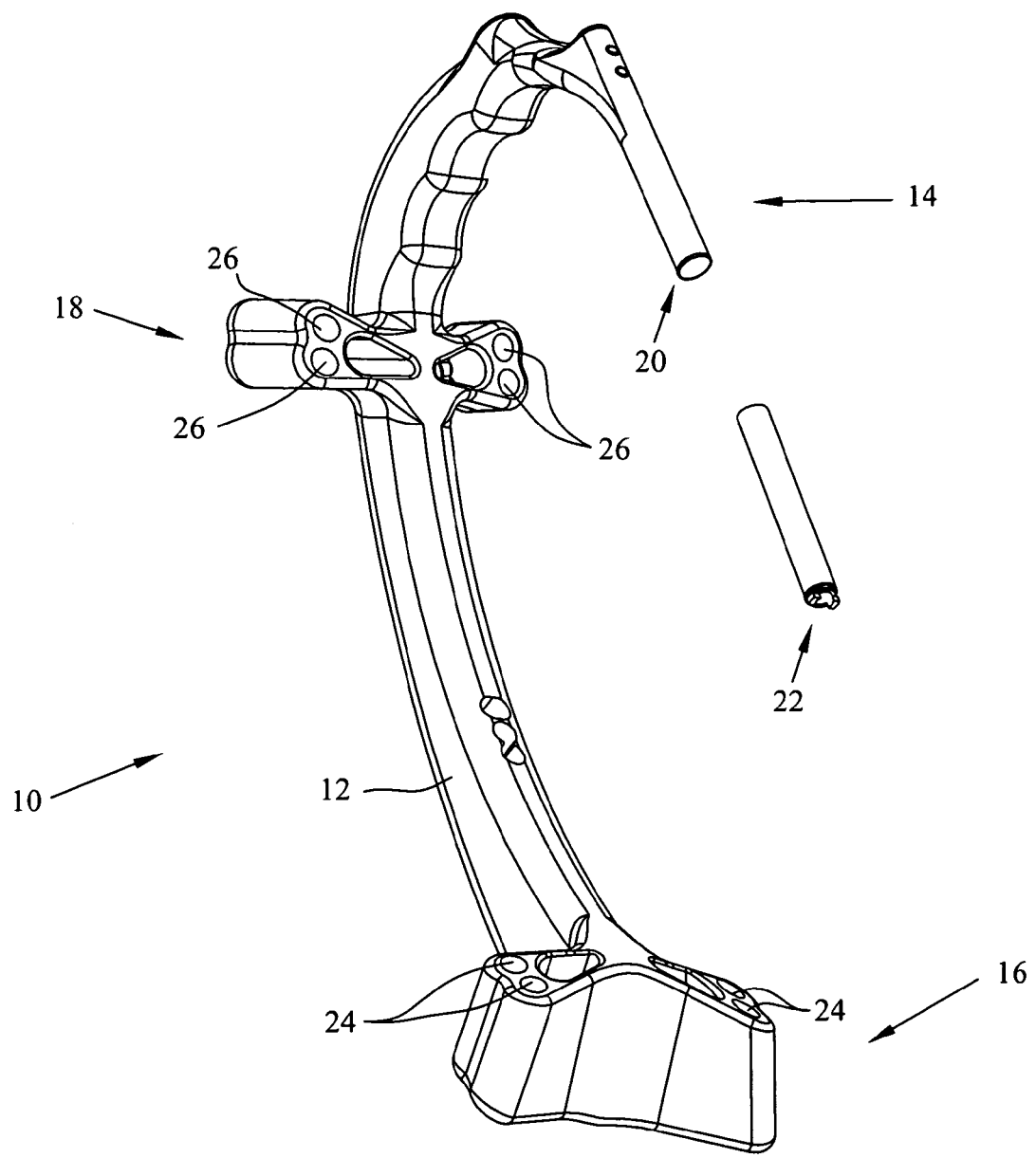
FIG. 2 is an exploded perspective view of the targeting device shown in FIG. 1.
Figure 3:
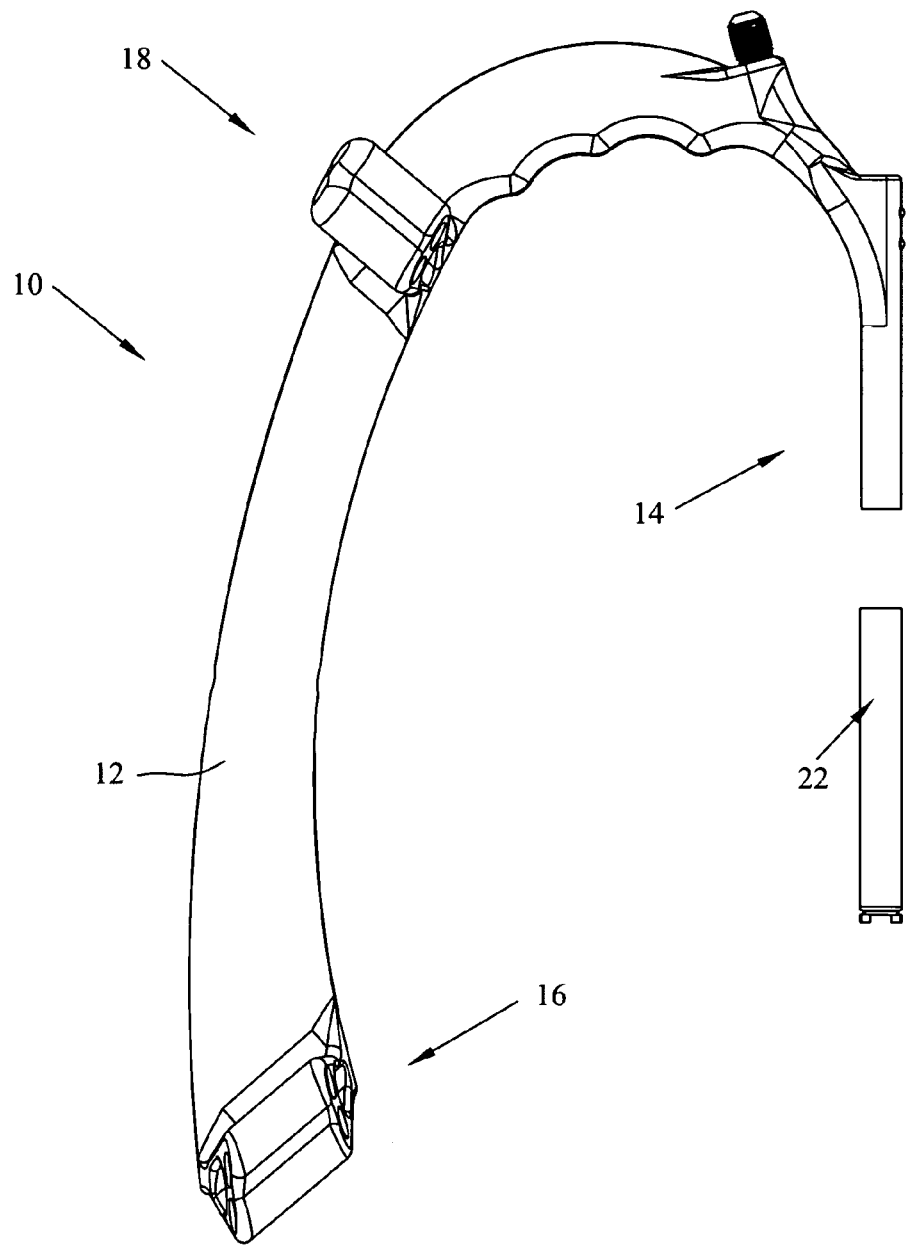
FIG. 3 is an exploded side view of the targeting device shown in FIG. 1.

FIGS. 1 through 3 depict a targeting device, generally indicated by numeral 10, representing an embodiment of the present invention. In the depicted embodiment, device 10 includes handle 12 which may be formed from any suitable radiolucent material, such as carbon reinforced polyetheretherketone (PEEK), for example. Handle 12 includes a nail engaging end 14 and a targeting end 16. In the depicted embodiment, handle 12 further includes an intermediate targeting portion 18. Nail engaging end 14 includes a receiving bore 20. Targeting device 10 also includes a guide barrel, generally indicated by numeral 22, sized and configured to be received within bore 20.

Targeting end 16 may include a plurality of throughbores 24. Similarly, intermediate targeting portion 18 may include a plurality of throughbores 26.

FIG. 4 shows a perspective view of guide barrel 22. In the depicted embodiment, guide barrel 22 includes a frame, generally indicated by numeral 28, and a sleeve 30. Frame 28 may be formed from any suitable material, such as stainless steel or titanium.

Frame 28 includes a reinforcing portion 32 and a nail interface 34. In the present embodiment, reinforcing portion 32 has a substantially cylindrical shape and includes a pair of recessed areas, or voids, 36. The cylindrical shape of reinforcing portion 32 defines a longitudinal bore indicated by numeral 33. Recessed areas 36 are formed in the side walls of reinforcing portion 32 on opposite sides of the longitudinal axis extending through the center of bore 33. The recessed areas 36 may be formed in any suitable manner, such as by way of laser cutting, and, as described below, facilitate viewing of components of the assembly during surgery in images taken during the surgery.

FIG. 5 depicts a close up view of nail interface 34. In the present embodiment, nail interface 34 includes a pair of impact surfaces 38 and a pair of prongs, each generally indicated by numeral 40. The impact surfaces 38 may have any profile desired, and each includes a substantially smooth surface.

In the embodiment depicted, the prongs 40 may be sized and configured as necessary to engage a mating portion of an intramedullary nail. Alternatively, the prongs 40 may be replaced with any suitable structure for engaging an intramedullary nail.

Referring again to FIG. 4, in the depicted embodiment, the sleeve 30 may be formed from any radiolucent material. For example, in the depicted embodiment, the sleeve 30 may be formed from a polyetheretherketone (PEEK). Other suitable radiolucent materials may also be utilized to form the sleeve 30.

Sleeve 30 may be attached to frame 28 in any suitable manner. For example, the sleeve 30 may be molded over the frame 28, or alternatively, sleeve 30 may be formed apart from frame 28, followed by insertion of frame 28 into the inner bore 31 of the sleeve 30.

Referring again to FIGS. 1 through 3, in the depicted embodiment, guide barrel 22 may be retained within throughbore 20 of handle 12 in a known manner. For example, handle 12 may be formed from injection molding, wherein the plastic material comprising handle portion 12 may be formed over a suitable attachment feature (not shown) of the guide barrel 22. In embodiments, the guide barrel 22 may be retained within the throughbore 20 of the handle 12 with an adhesive.

Figure 6:
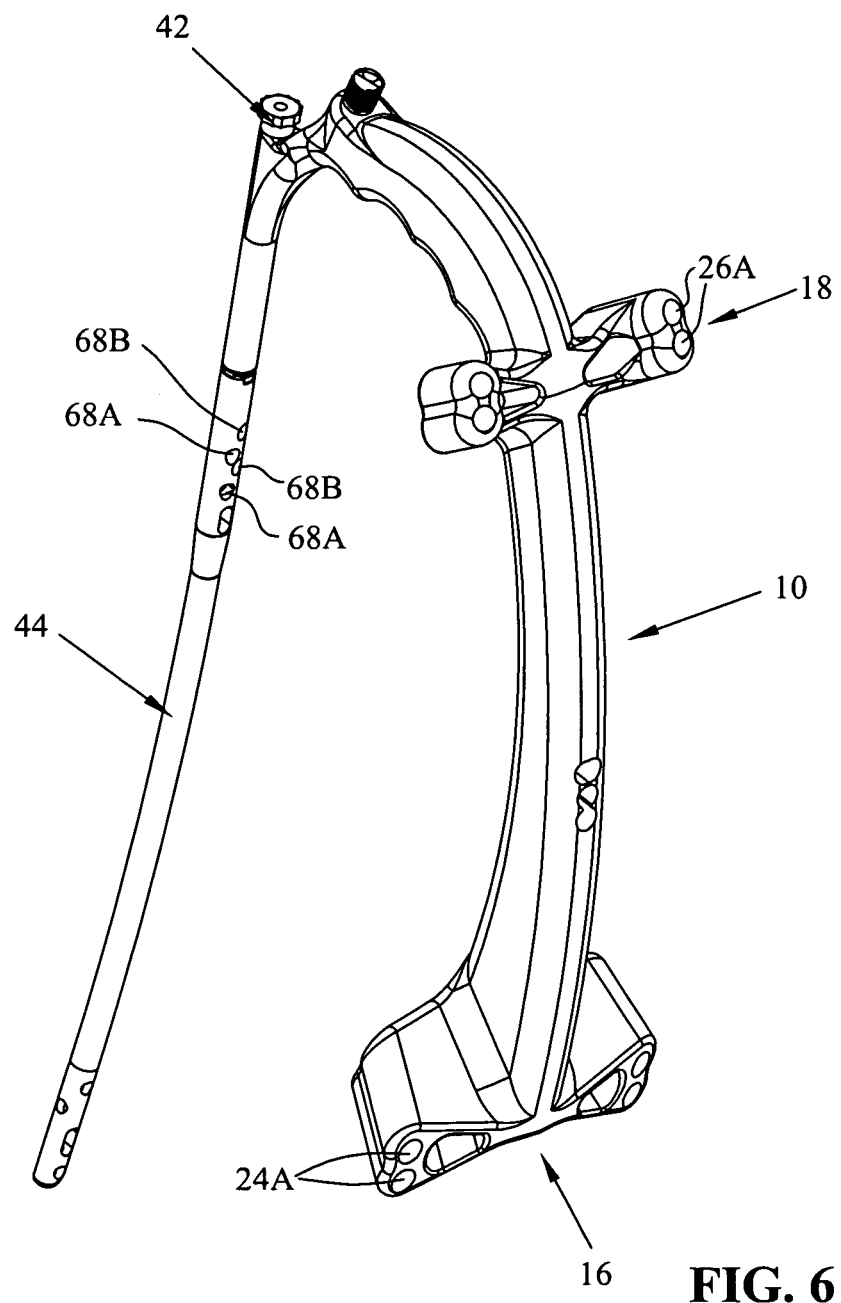
FIG. 6 is a rear perspective view of the device shown in FIG. 1 mating with an intramedullary nail.

FIG. 6 depicts targeting device 10 coupled via a locking bolt 42 to an intramedullary nail 44, which generally occurs prior to the insertion of the nail 44 into a intramedullary canal of a bone (not shown). Locking bolt 42 may be formed from any suitable biocompatible material, such as titanium or stainless steel. Similarly, intramedullary nail 44 may be formed from any suitable biocompatible material, such as titanium or stainless steel.

Figure 7:
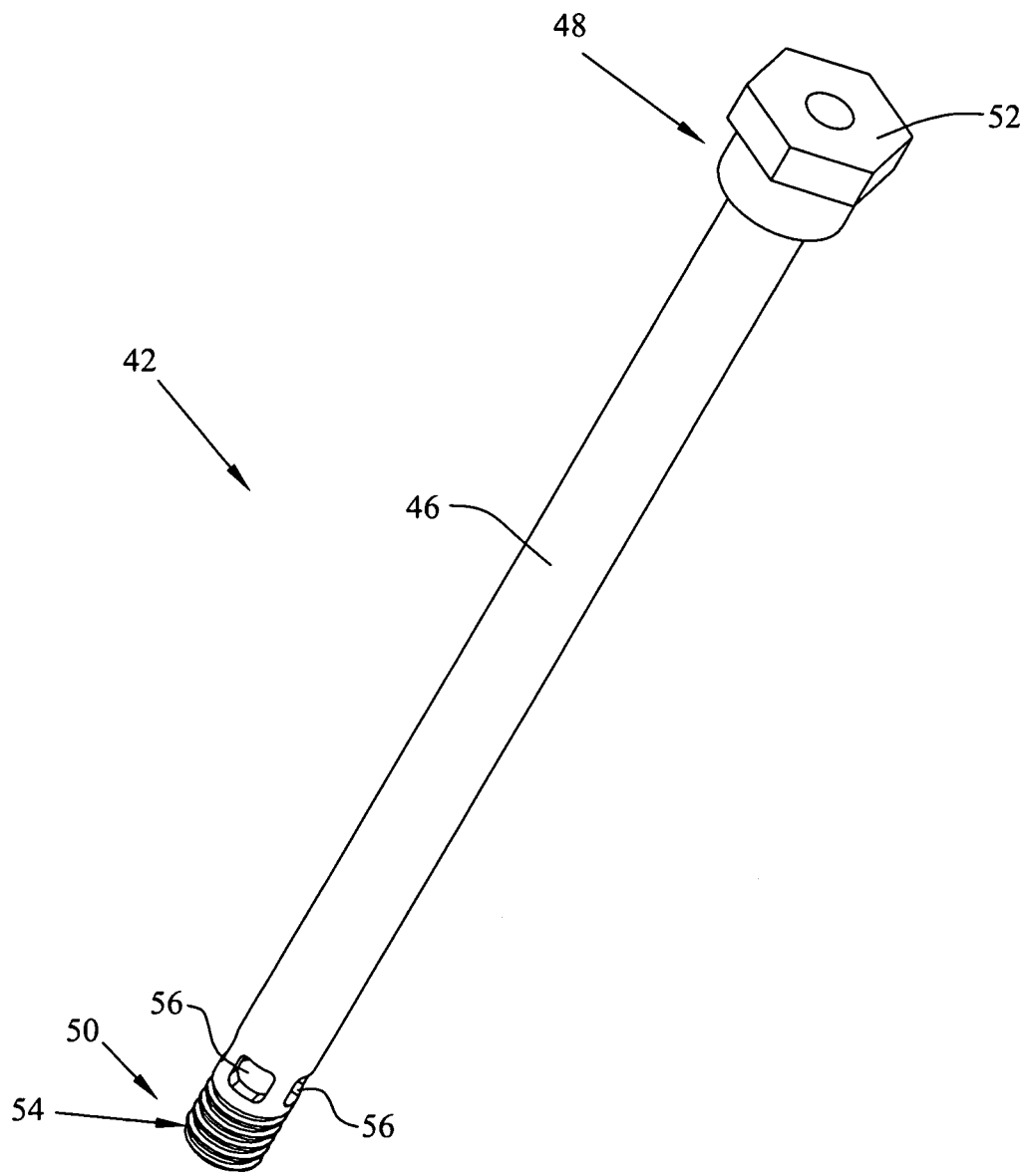
FIG. 7 is a perspective view of a locking bolt utilized in the device of FIG. 1.

FIG. 7 depicts a perspective view of locking bolt 42. Locking bolt 42 is being described for exemplary purposes only and may have other configurations as would be understood by one with skill in the art. Locking bolt 42 comprises a body portion 46 intermediate a first end 48 and a second end 50. In the present embodiment, body portion 46 has a cylindrical shape with a substantially smooth surface.

In the depicted embodiment, first end 48 includes a head 52. Head 52 may have any suitable configuration capable of engaging a known tool, such as a hexagonal profile configured for engagement by a wrench, for example. It should be noted that head 52 has a diameter larger than the diameter of body portion 46.

In the depicted embodiment, second end 50 includes a threaded portion, generally indicated by numeral 54. Second end 50 also includes a plurality of apertures, each indicated by numeral 56.

Figure 8:
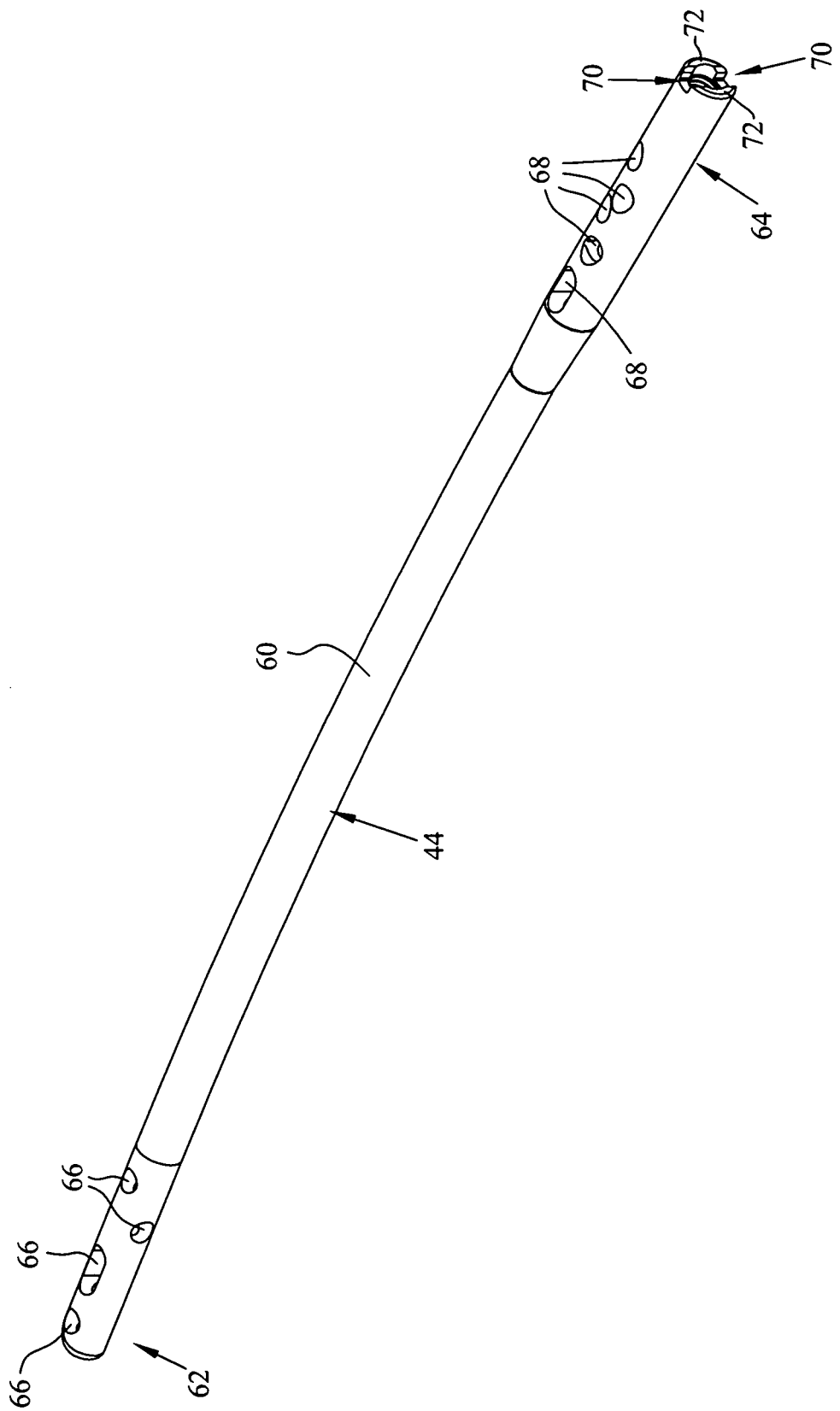
FIG. 8 is a perspective view of an intramedullary nail configured to mate with the targeting device of FIG. 1.

FIG. 8 depicts intramedullary nail 44. Nail 44 is being described for exemplary purposes only and may have any configuration known in the art. In the depicted embodiment, nail 44 includes a body portion 60 located intermediate first end 62 and second end 64. In the depicted embodiment, first end 62 includes a plurality of apertures, each indicated by numeral 66.

Figure 9:
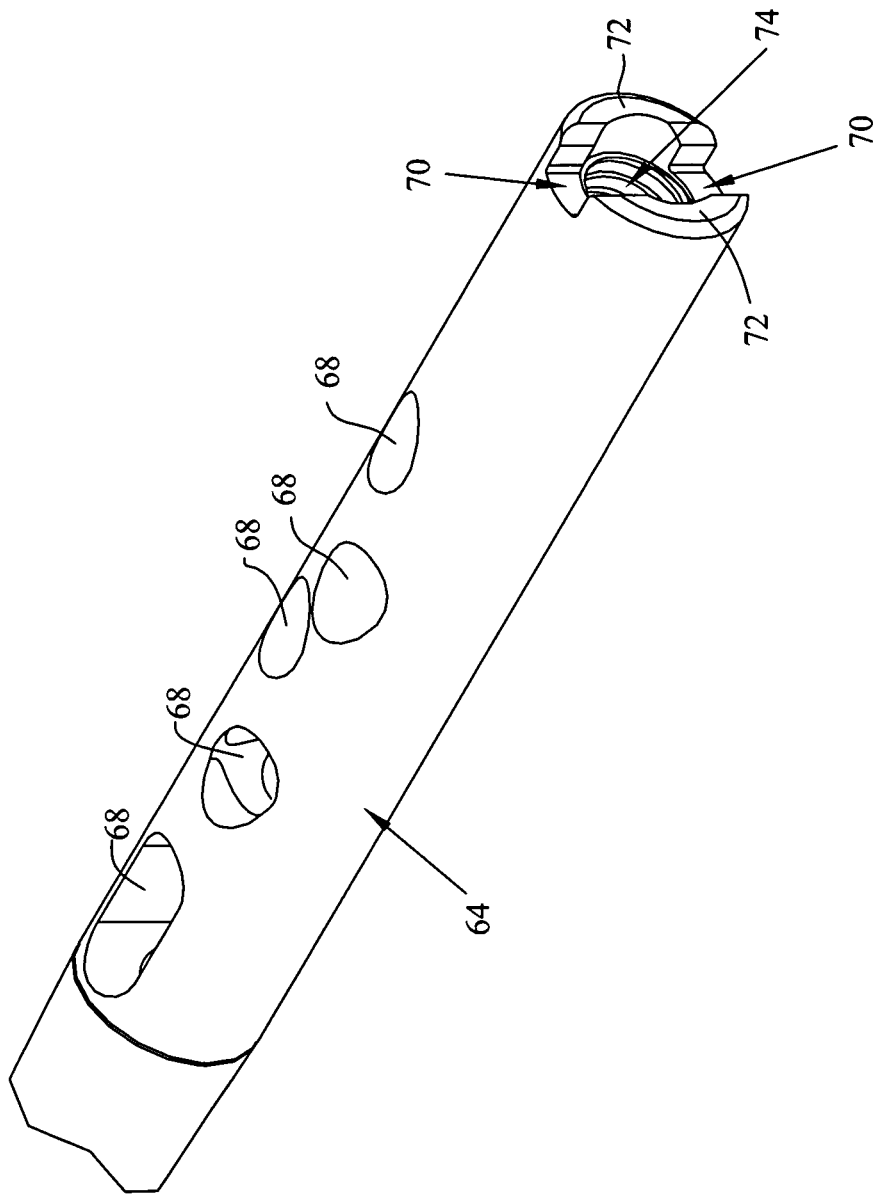
FIG. 9 is a enlarged fragmentary view of a portion of the nail shown in FIG. 8.

With reference to FIGS. 8 and 9, second end 64 includes a plurality of apertures 68. In addition, second end 64 includes a pair of notches, each indicated by numeral 70, a pair of flat surfaces, each indicated by numeral 72, and a threaded portion 74. In the depicted embodiment, notches 70 are sized to receive prongs 40 (FIG. 5). Similarly, surfaces 72 are sized complementary to surfaces 38 (FIG. 5). Threaded portion 74 is configured to mate with the threaded portion 54 of locking bolt 42.

With reference to FIGS. 6 through 9, in order to connect nail 44 to targeting device 10, the prongs 40 of guide barrel 22 are inserted into notches 70. Locking bolt 42 may then be inserted into bore 33 of guide barrel 22. When almost fully inserted, the threaded portion 54 of locking bolt 42 engages threaded portion 74 of nail 44. Since head 52 has a diameter greater than bore 33, the rotation of locking bolt 42 with draw nail 44 against guide barrel 22, as depicted in FIG. 6.

With reference to FIG. 6, when locking bolt 42 fully engages nail 44, throughbores 24A of targeting device 10 align with apertures 68A. Similarly, throughbores 26A of targeting device 10 align with apertures 68B.

Figure 10:
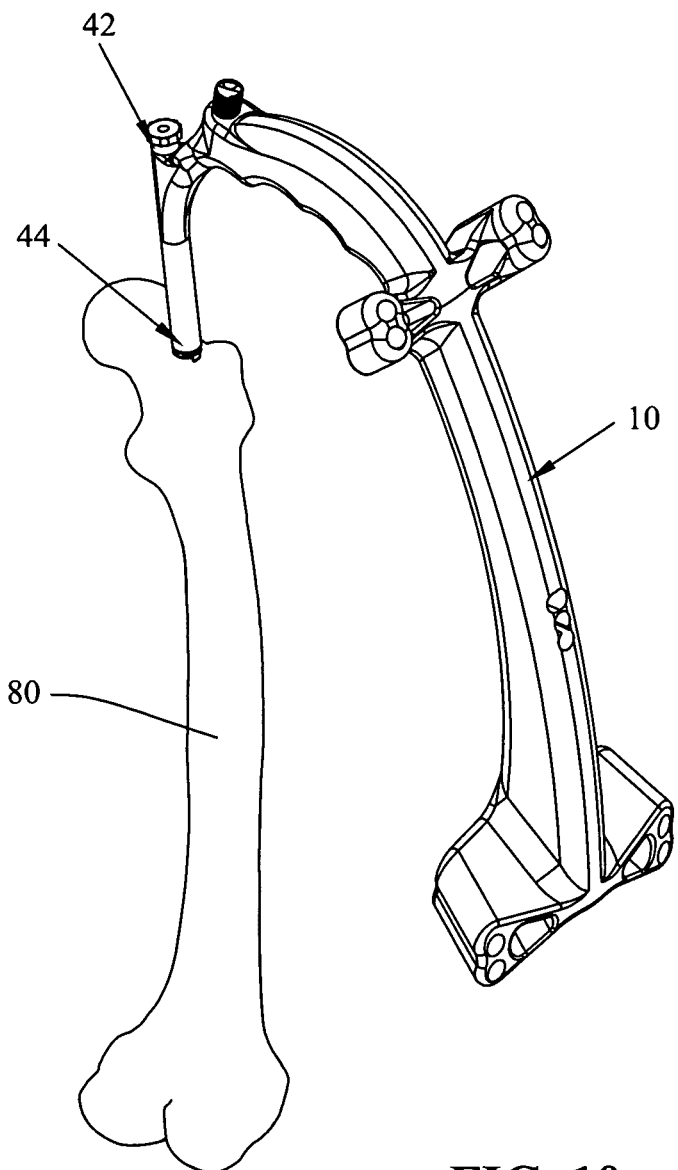
FIG. 10 is a perspective view showing the insertion into bone of an intramedullary nail attached to the targeting device shown in FIG. 1.

FIG. 10 depicts a nail 44 fully inserted into an intramedullary canal (not shown) of bone 80. In the depicted embodiment, the bore 80 is a femur. Nail 44 may be located within the canal in a known manner, and the surgical techniques for doing so are known in the art.

Figure 11:
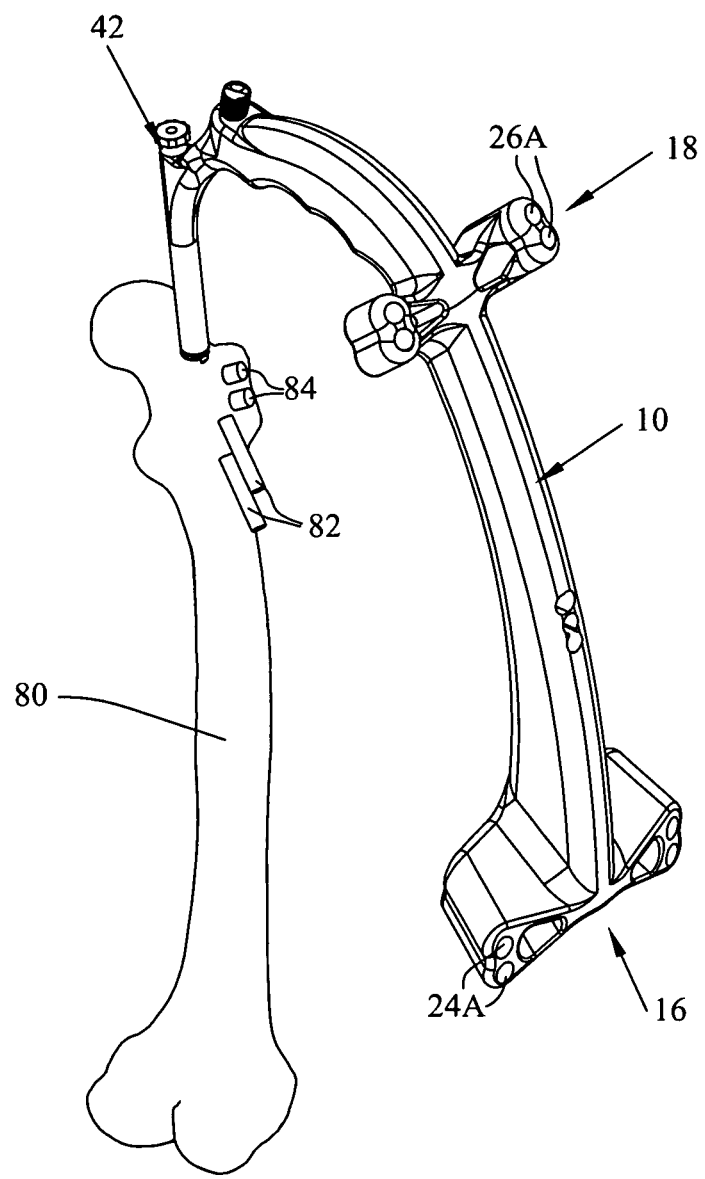
FIG. 11 is a perspective view of lag screws inserted into a bone and through the intramedullary nail connected to the targeting device shown in FIG. 1.

With reference to FIG. 11, once the nail 44 has been properly located within the canal of bone 80, lag screws 82, 84 may be inserted into the bone 80 in order to engage nail 44. Lag screws 82 align with throughbores 24A of targeting device and may be inserted into bone 80 and nail 44 in a known manner. Similarly, lag screws 84 align with throughbores 26A of targeting device 10 and may be inserted into bone 80 and nail 44 in a known manner.

Figure 12:
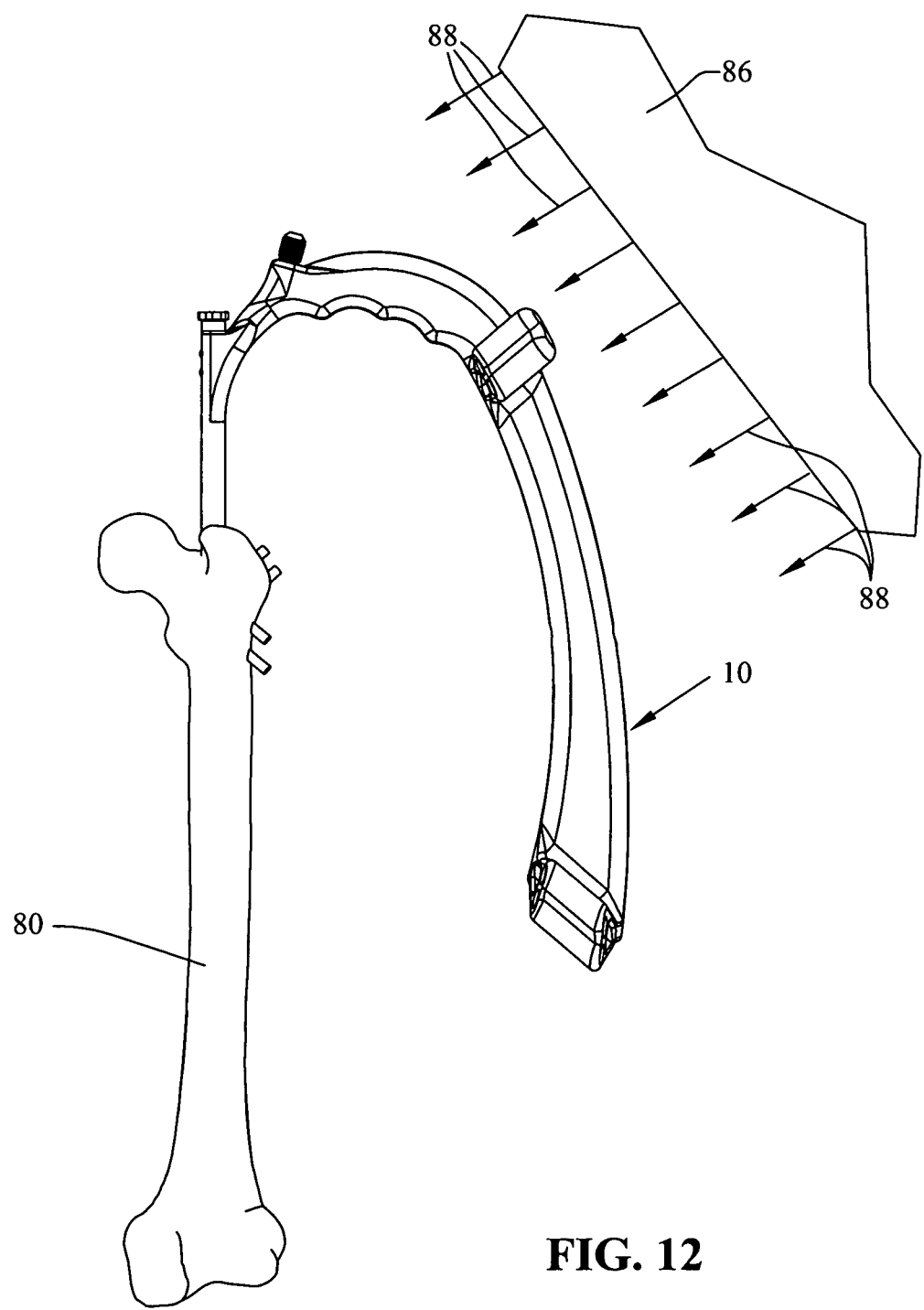
FIG. 12 is a side view of the view illustrated in FIG. 11, along with a schematic representation of an imaging device and orientation of the imaging device with respect to the targeting device.

FIG. 12 depicts a side view of the illustration depicted in FIG. 11. FIG. 11 schematically depicts an imaging device which, in one embodiment, may be a C-arm of a fluoroscopic imaging device, generally indicated by numeral 86, positioned in the area of the surgical technique. Arrows 88 represent an exemplary direction along which an image is obtained by the C-arm 86 during insertion of lag screws 84. Other types of imaging devices may also be used.

Figure 13:
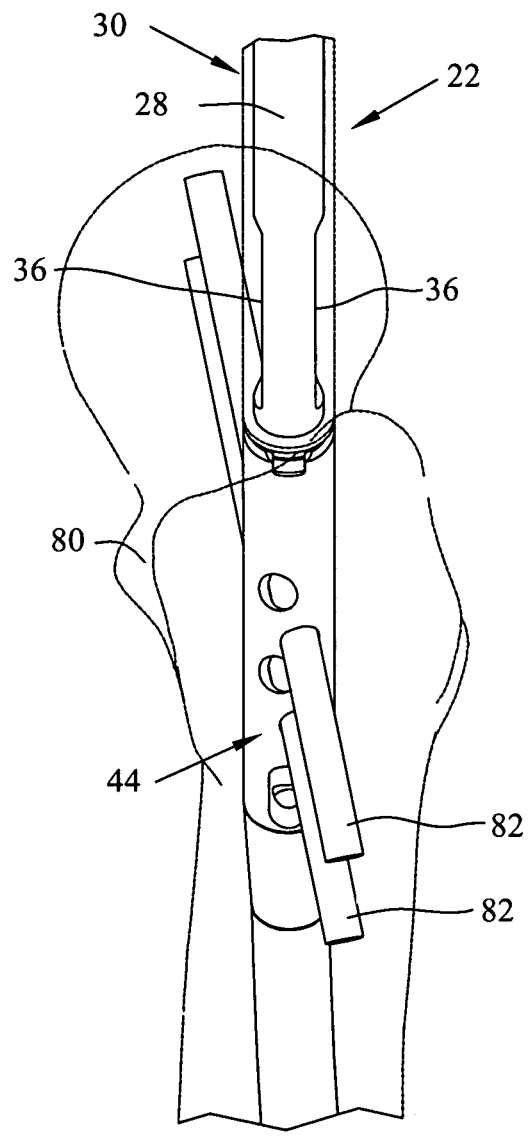
FIG. 13 is an exemplary view typical of that which would be generated by the imaging device in FIG. 12.

FIG. 13 depicts an image of the surgical area obtained by the C-arm prior to insertion of lag screw 84, as observed on a monitor (not shown). The C-arm 86 utilizes x-rays in order to generate the resulting images on the monitor. Since the handle portion 12 of targeting device 10 (FIG. 12) is manufactured substantially from a radiolucent material, the handle portion 12 will not be shown on the monitor and does not obstruct the view taken with the C-arm 86.

As shown in FIG. 13, a surgeon viewing on a monitor the image of the surgical area will be able to determine when the lag screws 82 are properly positioned within bone 80. The radiolucent sleeve 30 of the guide barrel 22 will not be seen in on the monitor when viewed using the C-arm 86. In FIG. 13, the radiolucent sleeve 30 is depicted in phantom for illustrative purposes only. Thus, it should be noted that since frame portion 28 of the barrel 22 is manufactured from a metal material, the frame portion 28 will remain visible even when viewed using the C-arm 86. Advantageously, recessed areas 36 provide a surgeon with some relief when attempting to view areas that would otherwise be obscured by the frame portion 28. In other words, the recessed areas 36 reduce the area masked by the frame portion 28 when the surgeon views the surgical area using the C-arm 86.

Figure 14:
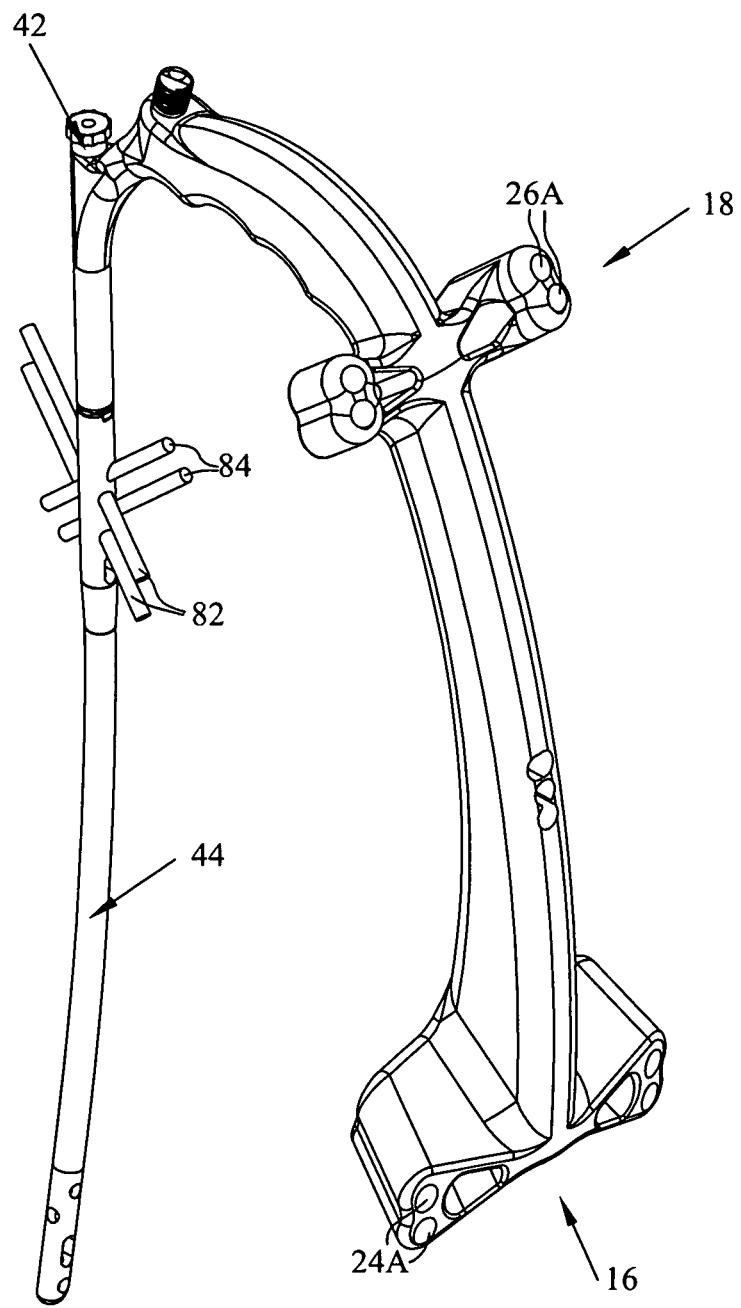
FIG. 14 is a depiction of FIG. 11 with the bone omitted for illustrative purposes.

FIG. 14 depicts the arrangement of FIG. 11 with bone 80 omitted for illustrative purposes. As can be seen in FIG. 14, lag screws 82 extend through apertures 68A (FIG. 6), and lag screws 84 extend through apertures 68B (FIG. 6).

Figure 15:
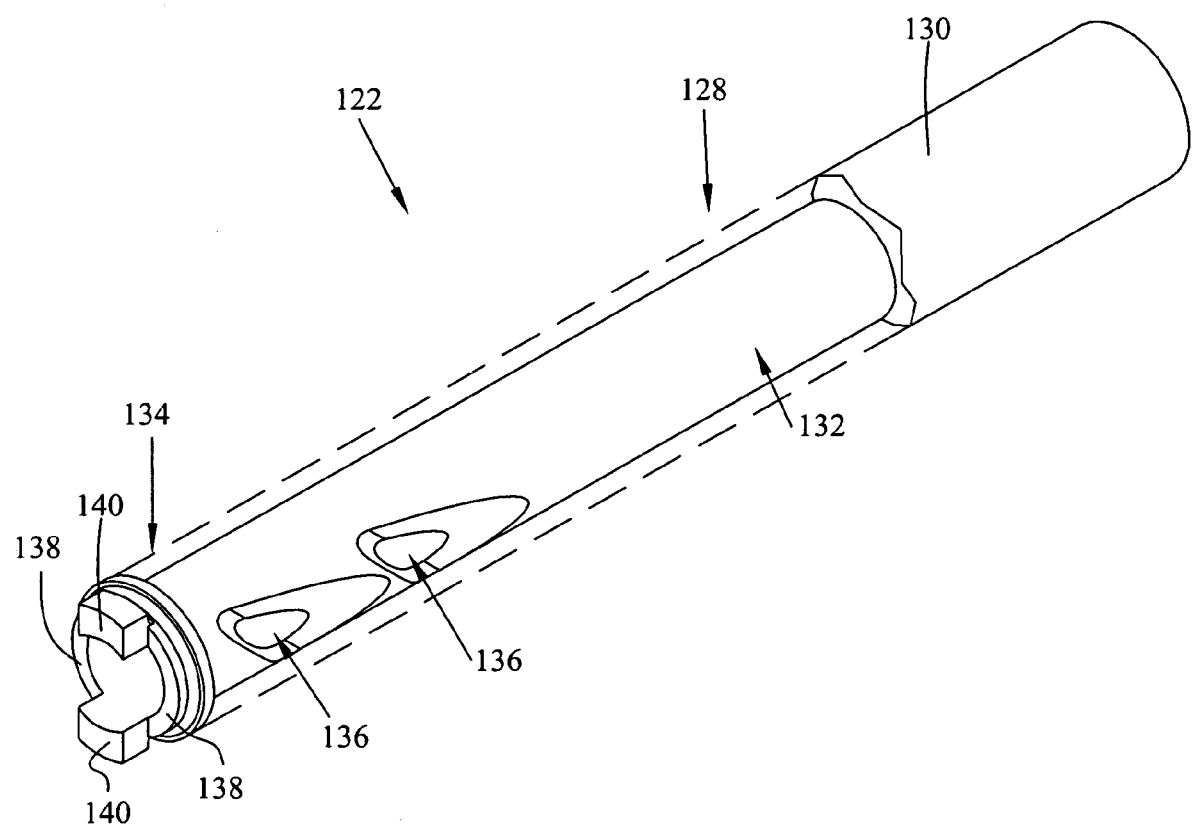
FIG. 15 is a perspective view of another embodiment of a guide barrel that may be utilized in the targeting device of FIG. 1.

FIG. 15 depicts another embodiment of a guide barrel, generally indicated by numeral 122. Guide barrel 122 includes a frame, generally indicated by numeral 128, and a sleeve 130. Frame 128 may be formed from any suitable material, such as titanium or steel, for example. Sleeve 130 may be formed from any suitable radiolucent material, such as PEEK, for example. For illustrative purposes, a portion of sleeve 140 has been omitted from the figure for illustrative purposes.

Frame 128 may be formed from any suitable material, such as titanium or steel. Frame 128 includes a reinforcing portion 132 and a nail interface 134. In the depicted embodiment, reinforcing portion 132 includes a plurality of recessed areas, each generally indicated by numeral 136. Reinforcing portion 132 has a substantially cylindrical shape.

Nail interface 134 includes impact surfaces 138. Each impact surface 138 is substantially flat. Nail interface 134 also includes prongs 140. The prongs 140 are sized and configured to engage an intramedullary nail.

Figure 16:
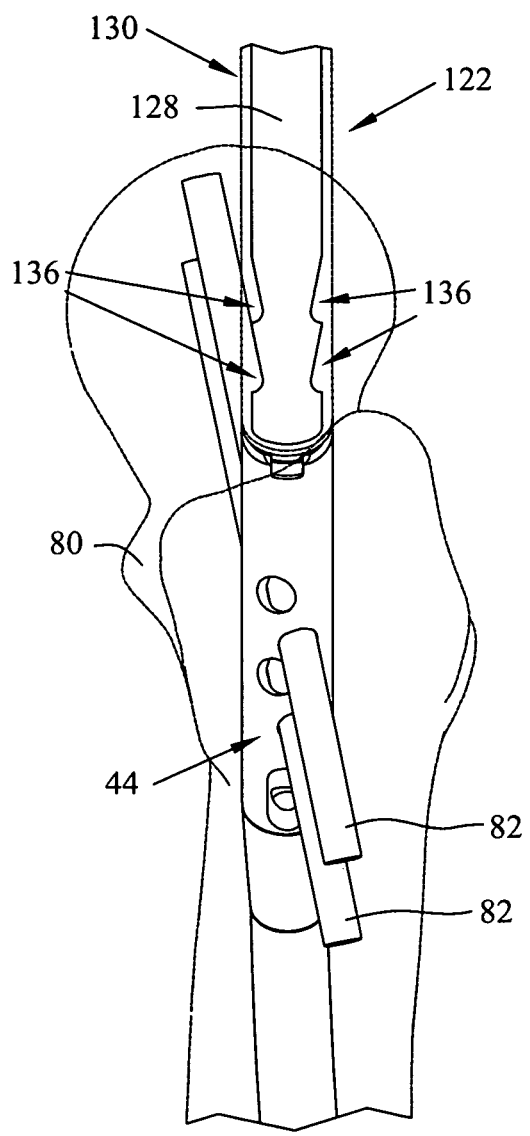
FIG. 16 is an exemplary view typical of that which would be generated by the imaging device in FIG. 12 including the barrel depicted in FIG. 15.

As shown in FIG. 16, a surgeon viewing on a monitor the image of the surgical area, similar to that illustrated in FIG. 13 incorporating the embodiment of the guide barrel 122 for guide barrel 22, will be able to determine when the lag screws 82 are properly positioned within bone 80. The radiolucent sleeve 130 of the guide barrel 122 will not be seen in on the monitor when viewed using the C-arm 86. In FIG. 16, the radiolucent sleeve 130 is depicted in phantom for illustrative purposes only. Thus, it should be noted that since frame portion 128 of the barrel 122 is manufactured from a metal material, the frame portion 128 will remain visible even when viewed using the C-arm 86. Advantageously, recessed areas 136 provide a surgeon with some relief when attempting to view areas that would otherwise be obscured by the frame portion 128. In other words, the recessed areas 136 reduce the area masked by the frame portion 128 when the surgeon views the surgical area using the C-arm 86.

FIGS. 17 and 18 depict another embodiment of a guide barrel 222. Guide barrel 222 includes a frame portion, generally indicated by numeral 228 and a sleeve 230. Frame 228 is generally formed from a metal material, such as steel or titanium. Sleeve 230 may be formed from any suitable radiolucent material, such as PEEK, for example. Sleeve 230 has been partially omitted from the figure for illustrative purposes.

Frame 228 includes a reinforcing portion 232 and a nail interface 234. In the depicted embodiment, reinforcing portion 232 has a substantially cylindrical shape and includes a plurality of openings 236. Openings 236 may be formed within reinforcing portion 232 in any suitable manner, such as by laser cutting.

Nail interface 234 includes impact surfaces 238. Nail interface 234 also includes prongs 240 sized and configured to engage an intramedullary nail.

In the depicted embodiment, nail interface 234 further includes recessed areas 242. The recessed areas 242 are located on opposite sides of the longitudinal axis of frame 228. Recessed areas 242 may be formed within frame 228 in any suitable manner. For example, recessed areas 242 may be laser cut into frame 228.

Figure 19:
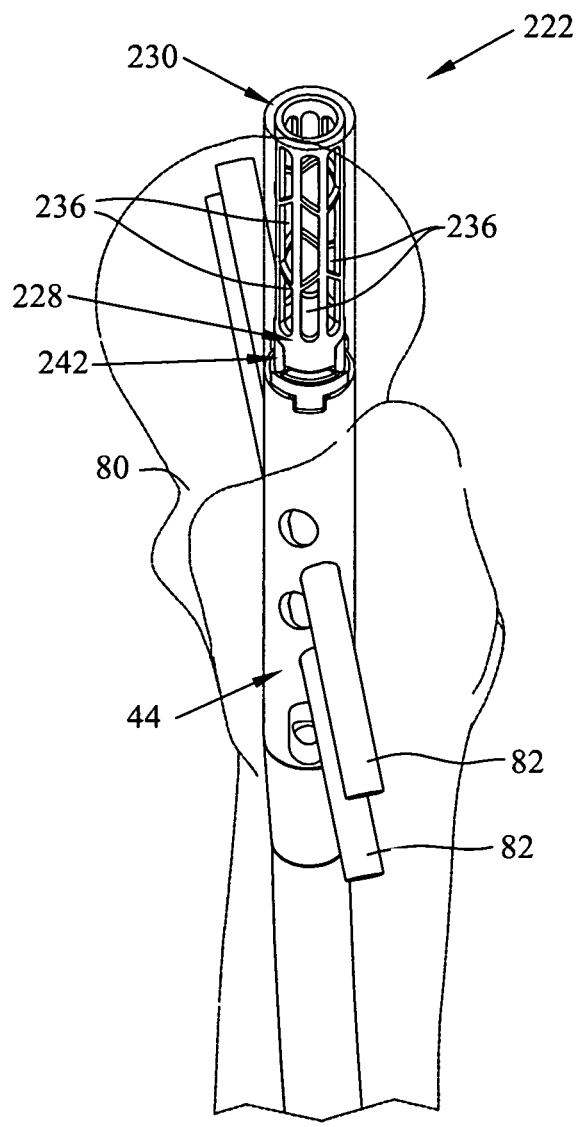
FIG. 19 is an exemplary view typical of that which would be generated by the imaging device in FIG. 12 including the barrel depicted in FIGS. 17 and 18.

As shown in FIG. 19, a surgeon viewing on a monitor the image of the surgical area, similar to that illustrated in FIG. 13 incorporating the embodiment of the guide barrel 222 for guide barrel 22, will be able to determine when the lag screws 82 are properly positioned within bone 80. The radiolucent sleeve 230 of the guide barrel 222 will not be seen in on the monitor when viewed using the C-arm 86. In FIG. 19, the radiolucent sleeve 230 is depicted in phantom for illustrative purposes only. Thus, it should be noted that since frame portion 228 of the barrel 222 is manufactured from a metal material, the frame portion 228 will remain visible even when viewed using the C-arm 86. Advantageously, recessed areas 236, 242 provide a surgeon with some relief when attempting to view areas that would otherwise be obscured by the frame portion 228. In other words, the recessed areas 136 reduce the area masked by the frame portion 228 when the surgeon views the surgical area using the C-arm 86.

Figure 20:
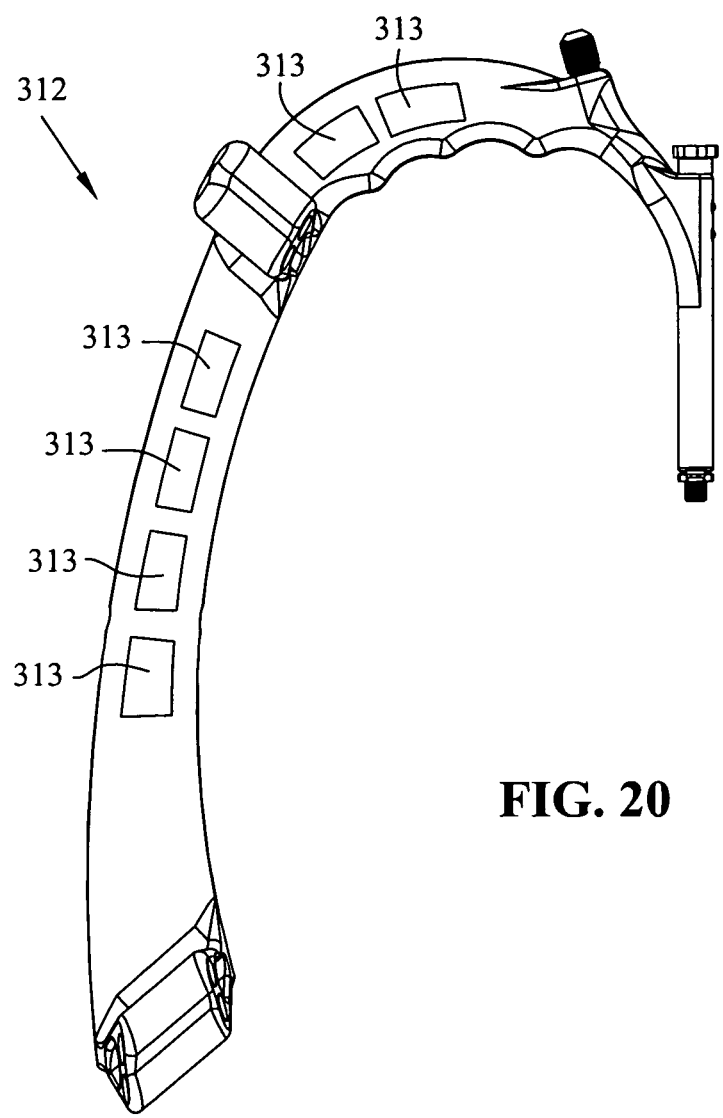
FIG. 20 is a side view of another embodiment of a targeting device.

FIG. 20 depicts another embodiment of a handle, generally indicated by numeral 312. In this embodiment, handle 312 has substantially the same configuration as handle 12. In addition, in the depicted embodiment, handle 312 includes a plurality of windows, each indicated by numeral 313. Windows 313 allow a surgeon to physically view through the handle 312 during surgery as needed.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A targeting device configured for connection to a proximal end of an intramedullary nail, said targeting device comprising:
   a handle member, said handle member having a nail engaging end including a throughbore; and a guide barrel connected to said handle member, said guide barrel including:
a frame having a side wall with an inner surface and an outer surface, said inner surface of said side wall defining a longitudinal bore in said frame, the longitudinal bore configured to be aligned with the throughbore of the handle member when the guide barrel is attached to the handle member, said frame having at least one opening in said side wall that extends from said outer surface to said inner surface of said side wall, wherein said frame includes a distal end including at least one prong configured to be at least partially received in a corresponding notch in the proximal end of the intramedullary nail, and at least one impact surface configured to impact a portion of the proximal end of the intramedullary nail, and
a sleeve at least partially encompassing said side wall of said frame, wherein at least a portion of said sleeve encompassing said side wall of said frame is located within said throughbore of said nail engaging end of said handle member.

2. The targeting device as set forth in claim 1 wherein at least a portion of said frame is comprised of metal, and at least a portion of said sleeve is comprised of a radiolucent material.

3. The targeting device as set forth in claim 2 wherein said radiolucent material is carbon reinforced polyetheretherketone (PEEK).

4. The targeting device as set forth in claim 1 wherein at least a portion of said handle member is comprised of a radiolucent material.

5. The targeting device as set forth in claim 1 wherein said handle member includes at least one targeting bore formed therein for aligning screws with apertures within the intramedullary nail.

6. A targeting device for use during insertion of an intramedullary nail into an intramedullary canal of a patient, said targeting device comprising:
a handle portion comprising a throughbore adapted to align with said intramedullary nail, said handle portion at least partially formed from at least one radiolucent material; and
means for connecting said handle portion with a proximal end of said intramedullary nail, said connecting means including a metal frame having a side wall with an inner surface and an outer surface, said inner surface of said side wall defining a longitudinal bore in said metal frame, the longitudinal bore configured to be aligned with the throughbore of the handle member when the guide barrel is attached to the handle member, said metal frame having at least one window opening in a portion of said side wall positioned along one side of said metal frame, said at least one window opening extending from said outer surface to said inner surface of said portion of said side wall, wherein said window opening has a closed loop boundary defined by said metal frame, the frame further including means for engaging said intramedullary nail, wherein said engaging means comprises at least one prong configured to be at least partially received in a corresponding notch in the proximal end of the intramedullary nail.

7. The targeting device as set forth in claim 6 wherein said handle portion includes a plurality of targeting bores for aligning screws with apertures within the intramedullary nail.

8. The targeting device as set forth in claim 6 wherein the at least one window opening is configured for visually determining a position of an upper boundary of said nail.

9. The targeting device as set forth in claim 6 wherein said connecting means further comprises a radiolucent sleeve around said metal frame.

* * * * *